(12) United States Patent
Helom et al.

(10) Patent No.: US 7,399,870 B2
(45) Date of Patent: Jul. 15, 2008

(54) SYNTHESIS OF PYRROLE-2-CARBONITRILES

(75) Inventors: Jean Louise Helom, Hillsdale, NJ (US); Arkadiy Zinoviy Rubezhov, West Nyack, NY (US); Anthony Scott Pilcher, Colchester, VT (US); Bogdan Kazimierz Wilk, New City, NY (US)

(73) Assignee: Wyeth, Madison, NJ (US)

( * ) Notice: Subject to any disclaimer, the term of this patent is extended or adjusted under 35 U.S.C. 154(b) by 501 days.

(21) Appl. No.: 11/086,061

(22) Filed: Mar. 22, 2005

(65) Prior Publication Data

US 2005/0222432 A1 Oct. 6, 2005

Related U.S. Application Data

(60) Provisional application No. 60/557,807, filed on Mar. 30, 2004.

(51) Int. Cl.
*C07D 207/30* (2006.01)
(52) U.S. Cl. .................................................. 548/561
(58) Field of Classification Search .................. 548/561
See application file for complete search history.

(56) References Cited

U.S. PATENT DOCUMENTS 5,204,332 A 4/1993 Brown et al. ................... 514/63
6,492,402 B1 12/2002 Lee et al. ..................... 514/365

OTHER PUBLICATIONS

Barnett, G. H. et al., "Pyrrole chemistry. XXI. Synthetic approaches to cyanopyrroles," *J. Can. Chem.* 1980, 58, 409-411.
Yoshida, K., "Regiospecific Anodic Cyanation of Pyrroles and Indoles," *J. Am. Chem. Soc.* 1977, 99, 6111-6113.
Yoshida, K., "Photosensitised Electron Transfer and Anodic Cyanation Reactions of Nitrogen Heterocyles," *J. Chem. Soc., Chem. Commun.* 1978, 1108-1109.
Saito, I. et al., "Trimethylsilyl Cyanide as a Trapping Agent for Dipolar Peroxide Intermediates," *J. Am. Chem. Soc.* 1985, 107, 5279-5280.
Tamura, Y. et al., "Cyanation using the Combined Reagent, Triphenylphosphine-Thiocyanogen (TPPT): A New General Route to Indole and Pyrrole Carbonitriles," *J. Chem. Soc., Perkin Trans. I* 1980, 1132-1135.
Anderson, H. J., "Pyrrole Chemistry. II. 2-Pyrrolecarbonitrile, 1-Methyl-2-Pyrrolecarbonitrile, and their Nitration Products," *Can. J. Chem.* 1959, 37, 2053-2058.
Chakrabarti, J. K. et al., "A New Route to Nitriles. Dehydration of Aldoximes using 2,4,6-Trichloro-s-triazine (Cyanuric Chloride)," *J. Chem. Soc., Chem. Commun.* 1972, 1226-1227.
Mlochowski, J. et al., Oxidative Conversion of N,N-Dimethylhydrazones Derived from Aliphatic and Heteroaromatic Aldehydes into Nitriles with Hydrogen Peroxide or 3-Chloroperoxybenzoic Acid, *J. Prakt. Chem.* 1994, 336, 467-469.
Fernández, R. et al., Simple and Efficient Conversion of N,N-Dimethylhydrazones and Aldehydes to Nitriles, *Tetrahedron Lett.* 1993, 34(1), 141-144.
Brückner, C. et al. "The Reductive Coupling of 2-Cyanopyrroles: A Study Pertaining to the Mechanism of Formation of Porphocyanines," *Tetrahedron*, 1998, 54, 2021-2030.
Capdevielle, P. et al., "Simple and Efficient Copper-Catalyzed One-Pot Conversion of Aldehydes into Nitriles," *Synthesis Communications*, Jun. 1989, 451-452.
Wang, N-C. et al., "Pyrrole chemistry. XVII. Alkylation of the pyrrolyl ambident anion," *Can. J. Chem*, 1977, 55, 4112-4116.
Loader, C. E. et al., "Pyrrole chemistry. XXIII. The cyanation of substituted pyrroles with chlorosulfonyl isocyanate (CSI). New syntheses of pyrrole-3-carbonitriles," *Canadian Journal of Chemistry*, 1981, 59, 2673-2676.
Vorbrüggen, H., "Reaktive Isocyanate I. Die Direkte Einfuehrung Von Nitril-Gruppen in Ungesattigte Systeme. Eine Einfache Umwandlung Von Carbonsäuren in Ihre Nitrile," *Tetrahedron Letters*, 1968, 9(13), 1631-1634.

*Primary Examiner*—Kamal A Saeed
(74) *Attorney, Agent, or Firm*—Woodcock Washburn LLP

(57) ABSTRACT

The instant invention concerns processes for the production of pyrrole-2-carbonitriles such as 1-methylpyrrole-2-carbonitrile. Such processes preferably comprise the steps of reacting a pyrrole with chlorosulfonyl isocyanate in the presence of a solvent and contacting the resulting product with a molar excess of an amide such as N,N-dimethylformamide. The product of this contacting step is then contacted with a molar excess of an organic base to produce a precipitate and a solution phase. The precipitate is then separated from the solution phase and the corresponding pyrrole-2-carbonitrile is isolated from the resulting solution phase.

17 Claims, No Drawings

SYNTHESIS OF PYRROLE-2-CARBONITRILES

CROSS-REFERENCE TO RELATED APPLICATIONS

This application claims priority to U.S. Application No. 60/557,807, filed on Mar. 30, 2004, the disclosure of which is incorporated by reference herein in its entirety.

FIELD OF THE INVENTION

The present invention is in the field of synthesis and isolation of pyrrole-2-carbonitriles such as 1-methylpyrole-2-carbonitrile.

BACKGROUND OF THE INVENTION

Pyrrole-2-carbonitriles are useful as intermediates in the production of chemical compounds, including pharmaceutical and insecticide compositions. See, for example, U.S. Pat. No. 6,492,402 (directed to thrombin inhibitors) and U.S. Pat. No. 5,204,332 (directed to pyrrole carbonitrile insecticidal, acaricidal and molluscicidal agents).

Barnett, et al., *J. Can. Chem.* 1980, 58, 409, teaches a synthetic process for 1-methylpyrrole-2-carbonitrile involving the reaction of 1-methylpyrrole with chlorosulfonyl isocyanate in dichloromethane in a first step. In Barnett's process, the product of the first step was reacted with DMF, and the reaction mixture was then poured into ice-cold 4M HCl. Following product workup and vacuum distillation, 1-methylpyrrole-2-carbonitile was said to be obtained in 58% yield.

Other synthetic methods for 1-methylpyrrole-2-carbonitrile from 1-methylpyrrole are said to include reaction with methanolic cyanide solution under anoidic oxidation conditions (*J. Am. Chem. Soc.* 1977, 99, 6111), reaction with excess 1,4-dicyanobenzene as a photosensitizer in the presence of methanolic cyanide solution (*J. Chem. Soc., Chem. Commun.* 1978, 1108), reaction of trimethylsilyl cyanide in a tetraphenylphorphine-sensitized photooxidation at −70° C. (*J. Am. Chem. Soc.* 1985, 107, 5279), and reaction with freshly prepared $Ph_3P(SCN)_2$ at −40° C. (*J. Chem. Soc., Perkin Trans. I* 1980, 1132). Another synthetic process starts with 2-pyrrolecarboxaldehyde (*Can. J. Chem.* 1959, 37, 2053 and *J. Chem. Soc., Chem. Commun.* 1972, 1226). Yet another process uses 2-pyrrolecarboxaldehyde as the starting material (*J. Prakt. Chem.* 1994, 336, 467 and *Tetrahedron Lett.* 1993, 34, 141). Such processes require tedious aqueous workup and repetitive extractions with ether, methylene chloride, or some other suitable solvent. Some procedures require the use of chromatography in the isolation/purification step.

SUMMARY OF THE INVENTION

In some aspects, the instant invention concerns a process for the production of pyrrole-2-carbonitriles such as 1-methylpyrrole-2-carbonitrile. A pyrrole is reacted with chlorosulfonyl isocyanate in the presence of a solvent that is substantially unreactive with chlorosulfonyl isocyanate and contacting the resulting product with a molar excess (preferably at least about 2.0 molar equivalents) of an N,N-dialkylformamide. This product is then contacted with a molar excess (preferably at least about 2.0 molar equivalents) of an organic base to produce a precipitate and a solution phase. The precipitate is then separated from the solution phase and the corresponding pyrrole-2-carbonitrile is isolated from the resulting solution phase. In some embodiments, water is added to the solution phase prior to isolating the pyrrole-2-carbonitrile. In certain embodiments, the pyrrole-2-carbonitrile is isolated by distillation.

In some embodiments, the solvent is toluene or acetonitrile. In certain of these embodiments, it is preferred that the solvent comprises toluene.

In other preferred embodiments, the N,N-dialkylformamide is N,N-dimethylformamide (DMF).

In certain embodiments, the base is a tertiary amine or an aromatic amine. In some preferred embodiments, the base is triethylamine.

In yet other embodiments, reaction of the pyrrole and the chlorosulfonyl isocyanate is performed at a temperature at or below about 0° C. In certain embodiments 0.1 to 0.4 molar equivalents of water per equivalent of the solvent is added to effect dilution. In certain preferred embodiments, the isolated solution phase is concentrated prior to its subsequent dilution and distillation.

In other aspects, the invention also concerns products that are made by the processes of the instant invention.

DETAILED DESCRIPTION OF ILLUSTRATIVE EMBODIMENTS

The instant invention relates to methods of producing pyrrole-2-carbonitriles, particularly 1-methylpyrrole-2-carbonitrile and preferably with improved isolated yields. In preferred embodiments, the methods of the invention involve reacting a pyrrole such as 1-methylpyrrole with chlorosulfonyl isocyanate. In certain embodiments, the molar ratio of pyrrole to chlorosulfonyl isocyanate is from about 0.9:1 to about 1.1:1, preferably approximately 1:1. It is also preferred that the reaction be preformed at or below about 0° C. The product of this reaction is then contacted with N,N-dialkylformamide, followed by the addition of an organic base.

The synthesis of 1-methylpyrrole-2-carbonitrile from 1-methylpyrrole is illustrated in Scheme I.

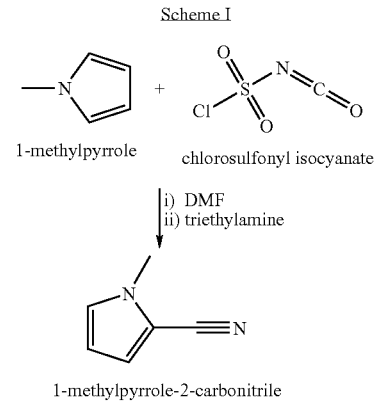

Although we do not intend to be bound by any particular theory or mechanism of operation, the N,N-dialkylformamide (such as N,N-dimethylformamide (DMF)) is believed to serve as a catalyst for the reaction. It is preferred that two equivalents of DMF be used in the instant process. During the reaction, DMF.HCl and $DMF.SO_3$ complexes are believed to be formed. By using a molar excess of DMF (preferably at least two equivalents), it is believed that one can avoid emission of the gaseous by-products HCl and $SO_3$.

Alkyl groups in N,N-dialkylformamides include aliphatic hydrocarbon chains having one to six, preferably one to four, and more preferably one to three carbon atoms, and includes, but is not limited to, straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. N,N-dialkylformamides also include cyclic compositions, e.g., where the cyclic group can have 5-7 ring members, such as six including N-formylpiperidine and N-formylmorpholine.

Organic bases useful in the instant invention include, but are not limited to, tertiary amines and aromatic amines. Tertiary amines include, but are not limited to, trimethylamine, triethylamine, tripropylamine, 1-methylpiperidine, 1,4-dimethylpiperazine, and N,N-diisopropylethylamine (Hunig's Base). Aromatic amines include, but are not limited to, pyridine, 2-picoline, 2,6-lutidine, quinoline, 5,6,7,8-tetrahydroquinoline. In some embodiments, triethylamine is preferred.

Solvents useful in the instant invention are those that are substantially unreactive with chlorosulfonyl isocyanate. These solvents include aliphatic hydrocarbons (such as heptane), aromatic hydrocarbons (such as toluene), chlorinated hydrocarbons (such as methylene chloride), chlorobenzene, dialkyl ethers (such as diisopropyl ether) and alkyl nitriles (such as acetonitrile). In some embodiments, toluene or acetonitrile are preferred. In other embodiments, toluene is preferred.

The pyrrole moiety is generally sensitive to acids and will form tar in their presence. In the instant process, the use of a molar excess of a base such as triethylamine ($Et_3N$) (preferably at least two equivalents), is believed to effect precipitation of a relatively pure, solid salt (e.g., $Et_3N.SO_3$) that can be removed by filtration. The filtrate (containing, e.g., $Et_3N.HCl$) can be worked up by aqueous extraction. Applicants have found that the triethylamine treatment increased the 31-41% yield reported by Barnett, et al., *J. Can. Chem.* 1980, 58, 409 to 65-76%.

Applicants have found that although one can distill the solution phase that is isolated following treatment with the organic base, in some embodiments, it is preferred to first add at least some water thereto, particularly when the distillation is performed at atmospheric pressure. While not wanting to be bound by theory, it is believed the addition of water breaks, for example, the toluene-nitrile complex. The addition of water has been found to allow separation of toluene from the product at a temperature of less than 85° C. In certain embodiments, 0.1 to 0.4 molar equivalent of water per equivalent of solvent is used.

This invention can be further illustrated by the following examples of the preferred embodiments thereof, although it will be understood that these examples are included only for illustration and comparison to the existing art, and are not intended to limit the scope of the invention unless specifically indicated.

EXAMPLE 1

A 5 liter flask was charged with acetonitrile (2.0 L) and 1-methylpyrrole (83 g, 3.5 mol). Chlorosulfonyl isocyanate (495 g, 3.5 mol) was added dropwise maintaining so as to maintain the reaction temperature at −6 to 0° C. It should be noted that chlorosulfonyl isocyanate is corrosive and reacts violently with water. After stirring for 15 min., N,N-dimethylformamide (DMF, 511 g, 7.0 mol) was added at −4 to 0° C. followed by triethylamine (707 g, 7.0 mol) and the stirring was continued at 10° C. The resulting white precipitate was filtered and washed with acetonitrile (200 mL). The filtrate was concentrated under reduced pressure. Water (4.0 L) was added to the residue, phases were separated and the aqueous phase was extracted with ethyl acetate (2×200 mL). The combined organic phases were washed with brine (3×500 mL). The organic phase was concentrated under vacuum and the residue was distilled using a Vigreux column at approximately 4 mm Hg/70±10° C. to give 1-methylpyrrole-2-carbonitrile (282 g, 76% yield).

EXAMPLE 2

Starting with 47.0 g of 1-methylpyrrole, the reaction was conducted in a manner generally analogous to Example 1 except that the acetonitrile was replaced with toluene. After addition of chlorosulfonyl isocyanate, two layers were formed. Upon cooling to 0 to 5° C., the bottom layer solidified. The hygroscopic solids were collected by filtration and washed with toluene. Concentration of the filtrates gave 325 mL of a toluene solution containing (as determined by 1H NMR) 0.55 mol of 1-methylpyrrole-2-carbonitrile (58.3 g, 95% yield).

EXAMPLE 3

A crude solution of 1-methylpyrrole-2-carbonitrile in toluene, produced as in Example 2, was washed with brine containing sodium hydroxide to remove traces of acids. The separated organic layer (673 g) was atmospherically distilled (head temperature 110-115° C.) to remove the bulk of the toluene. Water was added (255 mL total) and the distillation was continued until the head temperature started to increase to above 86° C. The pot residue (290 g), containing some water, was fractionally distilled under reduced pressure to give 1-methylpyrrole-2-carbonitrile (217 g).

All patents, patent applications, and other publications that appear in this application are incorporated herein in their entirety.

What is claimed is:

1. A process for preparing a pyrrole-2-carbonitrile comprising:
   (a) reacting a pyrrole with chlorosulfonyl isocyanate in the presence of a solvent;
   (b) contacting the product of step (a) with a molar excess of an N,N-dialkylformamide;
   (c) contacting the product of step (b) with a molar excess of an organic base resulting in the production of a precipitate and a solution phase;
   (d) separating the precipitate from the solution phase; and
   (e) isolating a pyrrole-2-carbonitrile from the solution phase of step (d).

2. The process of claim 1 wherein at least about 2.0 molar equivalents of an N,N-dialkylformamide are used in step (b).

3. The process of claim 1 wherein said organic base is a tertiary amine or an aromatic amine.

4. The process of claim 3 wherein at least 2.0 molar equivalents of a tertiary amine or aromatic amine are used in step (c).

5. A process according to claim 1 wherein the pyrrole-2-carbonitrile is isolated by distillation.

6. A process according to claim 1 wherein the pyrrole is 1-methylpyrrole.

7. A process according to claim 1 wherein the solvent is toluene or acetonitrile.

8. A process according to claim 1 wherein the solvent is toluene.

9. A process according to claim 3 wherein the tertiary amine is triethylamine.

10. A process according to claim 3 wherein the aromatic amine is pyridine.

11. A process according to claim 1 wherein the N,N-dialkylamide is N,N-dimethylformamide, N-formylpiperidine or N-formylmorpholine.

12. A process according to claim 1 wherein the N,N-dialkylformamide is N,N-dimethylformamide.

13. A process according to claim 1 wherein the molar ratio of the pyrrole to chlorosulfonyl isocyanate is from 0.9:1 to 1.1:1.

14. A process according to claim 5 wherein water is added to the solution phase prior to distilling the pyrrole-2-carbonitrile from the solution phase of step (d).

15. A process according to claim 14 wherein 0.1 to 0.4 molar equivalent of water per equivalent of solvent is utilized.

16. A process according to claim 15 wherein the solution phase of step (d) is concentrated prior to the addition of water in step (e).

17. A process according to claim 1 wherein step (a) is performed at a temperature at or below about 0° C.

* * * * *